United States Patent [19]

Spehr et al.

[11] Patent Number: 5,593,433
[45] Date of Patent: Jan. 14, 1997

[54] IMPLANTABLE ENDOCARDIAL LEAD WITH SELF-HEALING RETRACTABLE FIXATION APPARATUS

[75] Inventors: Paul R. Spehr, Lake Jackson; Mark M. Frankovich, Sugarland; Mark A. White, Friendswood, all of Tex.

[73] Assignee: Intermedics, Inc., Angleton, Tex.

[21] Appl. No.: 358,936

[22] Filed: Dec. 19, 1994

[51] Int. Cl.⁶ ........................................ A61N 1/05
[52] U.S. Cl. .......................... 607/128; 607/126; 607/127
[58] Field of Search .................. 607/126, 127, 607/128

[56] References Cited

U.S. PATENT DOCUMENTS

| | | | |
|---|---|---|---|
| 3,974,834 | 8/1976 | Kane | 128/418 |
| 4,146,036 | 3/1979 | Dutcher et al. | 128/418 |
| 4,538,623 | 9/1985 | Proctor et al. | 607/126 |
| 4,649,938 | 3/1987 | McArthur | 607/127 |
| 4,913,164 | 4/1990 | Greene et al. | 128/785 |
| 4,924,881 | 5/1990 | Brewer | 607/127 |
| 4,972,848 | 11/1990 | Di Domenico et al. | 607/127 |
| 4,988,347 | 1/1991 | Goode et al. | 606/1 |
| 5,011,482 | 4/1991 | Goode et al. | 606/1 |
| 5,013,310 | 5/1991 | Goode et al. | 606/1 |
| 5,020,545 | 6/1991 | Soukup | 607/127 |
| 5,056,516 | 10/1991 | Spehr | 128/419 P |
| 5,129,404 | 7/1992 | Spehr et al. | 128/785 |
| 5,421,348 | 6/1995 | Larnard | 128/772 |
| 5,447,534 | 9/1995 | Jammet | 607/127 |

FOREIGN PATENT DOCUMENTS

| | | | |
|---|---|---|---|
| 0414234 | 2/1991 | European Pat. Off. | A61N 1/05 |
| 0591053 | 4/1994 | European Pat. Off. | A61N 1/05 |

*Primary Examiner*—William E. Kamm
*Assistant Examiner*—Carl H. Layno
*Attorney, Agent, or Firm*—John R. Merkling

[57] ABSTRACT

An implantable endocardial lead with a retractable helix. A specialized stylet can be inserted into the lead at the proximal end and passed through the lead to the distal end. Located at the distal end of the lead is a piston supporting the helix. The piston is attached to a coiled trifilar conductor and has an electrode adjacent the helix. Immediately adjacent the piston proximally an additional first short coil of wire is interlocked between the wires of the trifilar conductor, providing a female thread within the conductor. The stylet has a second single strand short coil segment spot welded to the stylet adjacent a distal end thereof. The stylet is rotated to screw the second short coil segment on the stylet into the first short coil adjacent the piston.

12 Claims, 2 Drawing Sheets

IMPLANTABLE ENDOCARDIAL LEAD WITH SELF-HEALING RETRACTABLE FIXATION APPARATUS

BACKGROUND OF THE INVENTION

1. Field of Our Invention

The present invention relates generally to cardiac stimulation, and more particularly to an implantable endocardial lead for stimulation or sensing electrical activity of the heart in connection with an implantable pacemaker. The lead employs a retractable fixation mechanism which can be repeatedly exposed to or shielded from tissue during the process of securing the lead to cardiac tissue.

2. Description of the Prior Art

There are generally two types of body implantable leads used with cardiac pacemakers—one which requires surgery to expose the myocardial tissue to which an electrode is affixed and another which can be inserted through a body vessel, such as a vein, into the heart where an electrode contacts the endocardial tissue. In the latter type, the endocardial lead is often secured to the heart through the endothelial lining by a helix affixed to a distal end of the lead. When the end of the lead contacts the lining of the heart at a desired location, the lead may be secured in place by rotating the lead, thus screwing the helix into the heart tissue.

A helix system has been relatively effective in securing an endocardial lead once the initial location of the lead has been achieved. However, it is undesirable to expose the helix while the lead is being inserted through a blood vessel into the heart. Moreover, it is difficult to precisely place an endocardial lead on the first attempt. It is common for a physician to repeatedly attempt to place an endocardial lead having a helix securing means. It is desirable, therefore, to be able to shield the helix during the insertion of the lead through the vein and between attempts to implant the lead on the heart lining. In the prior art, various apparatus have been proposed for achieving the desired result. For example, U.S. Pat. No. 3,974,834 to Lawrence M. Kane, discloses an implantable intervascular lead having an accordion-fold sleeve surrounding a helix. The sleeve is retractable to expose the helix and re-expandable to cover the helix in the event the helix is unscrewed and withdrawn. An object of the invention is to permit the lead to be inserted into and guided through a body vessel without snagging the body vessel.

Another attempt at solving these problems is disclosed in U.S. Pat. No. 4,146,036 to Robert G. Dutcher and Albert S. Benjamin. This patent discloses a body implantable, intervascular lead, having a helix fixation means. Apparatus for shielding the helix comprises a moveable piston or shaft located within the coils of the helix. The shaft is spring-loaded in a retracted position by the action of an elastomeric boot which also serves to seal off body fluids from the interior of the lead. A stylet passes through a lumen in the lead and acts against a proximal end of the shaft to force the shaft forward through the helix thus forming a partial barrier and inhibiting the helix from coming in contact with tissue, at least in the axial direction.

In U.S. Pat. No. 4,649,938 to William A. McArthur, an endocardial lead with an extendible/retractable helix fixation means is described. The helix is mounted on a bobbin carried within the electrode tip. The bobbin and helix are retracted into the electrode tip by the action of a spring and are extended out of the tip by pressure from the end of the stylet inserted through a lumen in the lead.

In U.S. Pat. No. 5,056,516 to Spehr, one of us, described an endocardial lead with a flexible, tubular lanyard. The lanyard passed through a lumen from a proximal end of the lead to a distal end of the lead, where the lanyard was attached to a sliding member supporting a helix. When the helix was in an exposed position, torque could be transmitted from the proximal end of the lanyard to the distal end thereof through a piston and thence to the helix to screw the helix into the endocardial tissue. To stiffen the lead during implantation, a stylet could be inserted into the lumen in the lanyard. The invention of this later patent has been assigned to the same assignee as our present invention. The patent was designated as an improvement on an invention of Bradshaw, assigned to our same assignee and disclosed in U.S. Pat. No. 4,913,164.

A removable lanyard and stylet was disclosed by Spehr and Foster in U.S. Pat. No. 5,129,404. Brewer described a lead with a removable threaded stylet in U.S. Pat. No. 4,924,881. Both of these patents are also assigned to our assignee.

SUMMARY OF OUR INVENTION

The present invention provides an implantable endocardial lead with retractable fixation means. In the preferred embodiment, the fixation means comprises a helix which can be repeatedly both retracted within a distal end of the lead and displaced outside the distal end of the lead. The lead defines a lumen from its proximal to its distal end. A specialized stylet can be inserted into the lumen at the proximal end and passed through the lead to the distal end. Located at the distal end of the lead is a piston supporting the helix. The piston is preferably, but not necessarily, constrained to slide along the axis of the lead. The piston is attached to a coiled trifilar conductor and has an electrode adjacent the helix. Immediately adjacent the piston proximally an additional first short coil of wire is interlocked between the wires of the trifilar conductor. The short coil has about five to ten turns proximally from the piston and a smaller diameter than the trifilar conductor.

The stylet comprises a wire having a distal end or tip. Preferably, the distal tip has a slightly reduced section adjacent to the tip which is more flexible than the remaining stylet. Adjacent this section, we have attached a second single strand short coil segment. This coil segment is spot welded to the stylet. In operation, the stylet is inserted into the lead and rotated to screw the second short coil segment on the stylet into the first short coil adjacent the piston. The piston can then be pushed by the stylet to expose the helix, or pulled by the engagement of the two short coils to withdraw the helix into the distal end of the lead. If too much tension is placed on the piston through the stylet, the short coils will disengage by the first coil being forced between the wires of the trifilar conductor. When the stylet is withdrawn so that the distal end does not overlap the first short coil, the first short coil will again collapse to its smaller diameter, thus making the apparatus self-healing. The stylet can then be rethreaded into the first short coil.

It is a principal object of our present invention to provide an implantable endocardial lead with retractable fixation means wherein the fixation means can be repeatedly shielded and exposed during the implantation process.

A further object of our invention is to provide a lead wherein the fixation means is selectively shielded within a distal end of the lead and wherein the fixation means is selectively exposed and shielded by the action of a removable stylet.

Another object of our invention is to provide an implantable lead with a retractable fixation means which is self-healing.

These and other objects and features of our invention will be apparent from the detailed description taken with reference to the accompanying drawings.

DETAILED DESCRIPTION OF OUR PREFERRED EMBODIMENT

Figure 1:
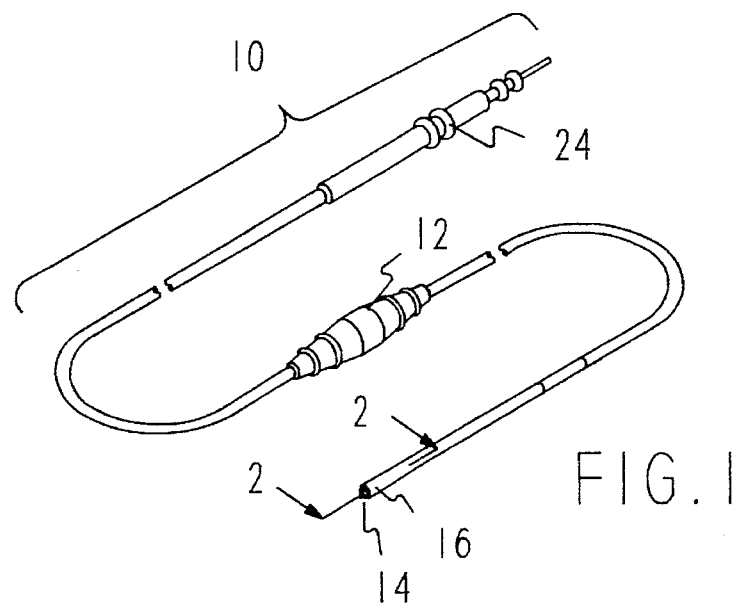
FIG. 1 is a prospective view of an implantable endocardial lead according to our invention.

Reference is now made to the drawings, wherein like numerals designate like parts throughout. FIG. 1 shows an endocardial lead, generally designated 10. The lead 10 has a suture sleeve 12 which slides along the lead 10 and which can be attached at an entrance into a vein of a patient in a conventional manner. The lead 10 also has an electrode 14 located at a distal end 16 of the lead.

Figure 2:
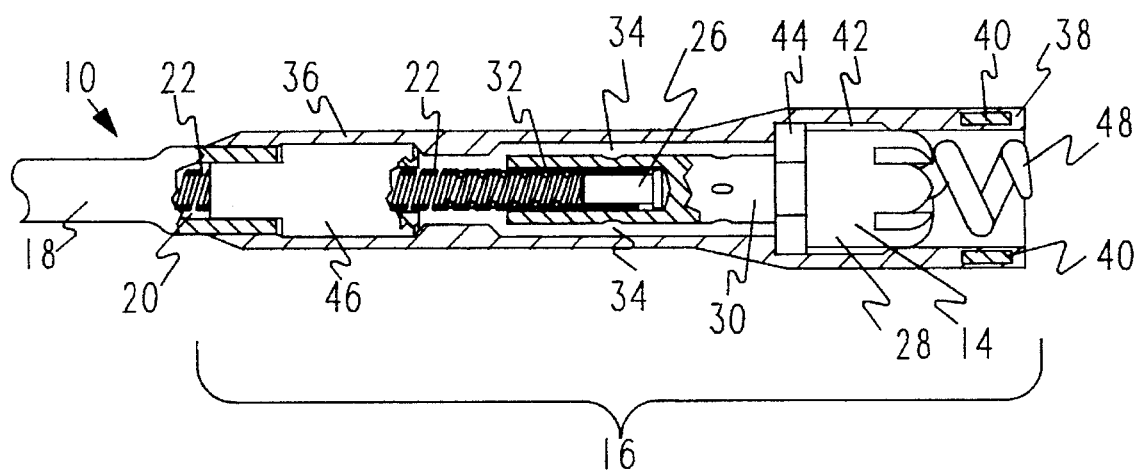
FIG. 2 is a sectional view of a distal tip of the lead taken along line 2—2 of FIG. 1.

As shown in FIG. 2, the lead 10 comprises a polyurethane sheath or catheter 18 which defines a lumen 20 along a longitudinal axis of the lead 10. Within the lumen 20, there is a coil conductor 22 for transmitting electrical impulses between the electrode 14 and a proximal end 24 of the lead 10. In the illustrated embodiment, a trifilar conductor is shown as the coil conductor 22. The coil conductor 22 wraps around a crimp plug 26 at the distal end 16 of the lead 10.

Figure 4:
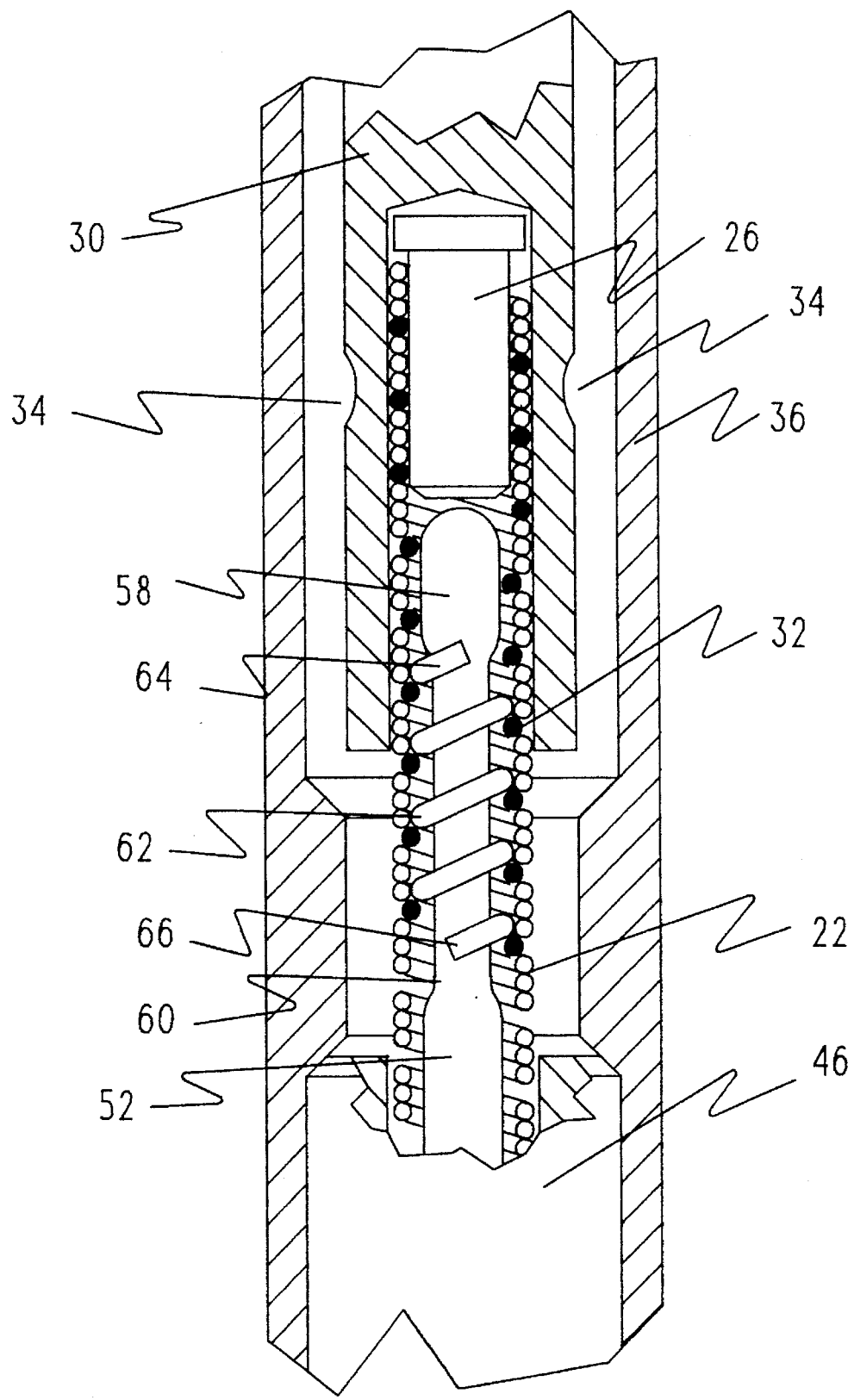
FIG. 4 is an enlarged sectional view of a portion of the distal tip of FIG. 2 with the stylet of FIG. 3 inserted therein.

The electrode 14 comprises a contact 28 and a conductive sleeve 30. The conductive sleeve 30 fits over the crimp plug 26 and the coil conductor 22. A first single strand short coil segment 32 is interposed between the coils of the trifilar conductor 22 and adjacent crimp plug 26. As can best be seen in FIG. 4, the short coil segment 32 has a smaller normal interior diameter than does the trifilar conductor 22. This causes the short coil segment 32 to effectively form a thread within the trifilar conductor 22. The short coil segment 32 extends along the crimp plug 26 and for preferably between five and ten turns proximally from the crimp plug 26. The four elements just mentioned are secured together by a crimp 34 in the conductive sleeve 30.

A silicone rubber sheath 36 houses the electrode 14. The silicone rubber sheath 36 comprises a distal edge 38 which is open to allow the electrode to be exposed. Near the distal edge 38 is a radiopaque ring 40 which is useful to a physician in placing the lead 10 within the heart of the patient. Proximal from the radiopaque ring 40 is an hexagonal chamber 42. The hexagonal chamber 42 houses a male hexagonal piston 44. The silicone rubber sheath 36 is connected to the polyurethane sheath 18 by a polyurethane splice tube 46. The silicone sheath 36 is glued to the polyurethane sheath 18 and the polyurethane splice tube 46 with silicone medical adhesive. Polyurethane adhesive bonds the polyurethane sheath 18 to the polyurethane splice tube 46.

In the illustrated embodiment, a fixation means is illustrated by a helix 48. The piston 44 and contact 28 support the helix 48 in relatively constant alignment along the longitudinal axis of the lead 10. The piston 44 slidably engages the hexagonal chamber 42 of the silicone sheath 36. In our preferred embodiment, the hexagonal chamber 42 and the hexagonal piston 44 permit the helix 48 to be rotated by rotating the entire lead. However, it is equally possible to omit this feature and permit the piston to rotate inside the electrode. Torque would be applied to the helix through a stylet, to be described hereafter. Such a configuration would be especially well adapted for use in atrial leads, which frequently have a "J" shape which prevents the entire lead from being turned.

Figure 3:
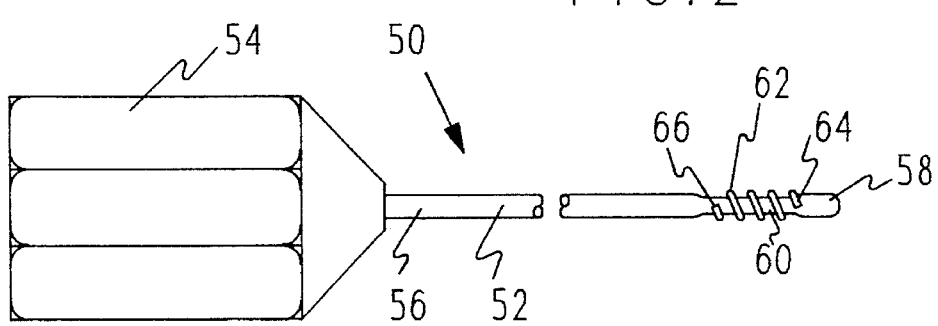
FIG. 3 is a plan view of a stylet for use with the lead of FIG. 1.

A stylet 50 is illustrated in FIG. 3. The stylet 50 comprises a stylet wire 52. The stylet wire 52 has a handle 54 at a proximal end 56. A distal end 58 is inserted into the lead 10. Adjacent the distal end 58 is a reduced diameter segment 60 which renders the stylet wire 52 slightly more flexible distally. A second single strand coil segment 62 of wire is wound along the reduced segment 60. The single strand coil segment 62 has a distal end 64 and a proximal end 66. These ends 64, 66 are attached to the stylet, preferably by welding. The second coiled segment 62 has a similar pitch and inner diameter as the first short coil segment 32. The second coil segment 62 is preferably about 4 or 5 coils long. The first short segment 32 and the second coil segment 62 thus form female and male threads respectively. Clearly, the short coil segment 62 could be replaced by actual threads, as suggested by Brewer, U.S. Pat. No. 4,924,881.

The two short coil segments 32, 62 can threadably engage each other. The stylet 50 passes through the coil 22 within the lumen 20 from the proximal end 24 to the distal end 16 of the lead 10. The distal end 58 of the stylet can then be threaded into the short coil segment 32. By pushing on the stylet a physician can expose the helix 48 outside of the distal end 16 of the lead 10. By pulling on the stylet, the helix 48 can be withdrawn within the lead 10. If excessive force is used to withdraw the helix 48, the first short coil segment 32 will be expanded into the trifilar conductor 22. However, as soon as the distal end 58 of the stylet has disengaged from the first coil segment 32, the first coil segment 32 will resume its previous smaller diameter, thus making this apparatus self-healing. During implantation, the helix 48 can be repeatedly moved into and out of the distal end 16 of the lead 10 until proper placement has been achieved. Then the physician can withdraw the stylet 50. The stylet 50 can be replaced in the lead or withdrawn therefrom as often as desired. It can also be replaced in the lead after the lead has be implanted for a period of time, should it become necessary to reposition the lead and if it is desired to retract the helix within the lead.

Our invention may be embodied in other specific forms without departing from the spirit or essential characteristics thereof. The present embodiment is therefore considered in all aspects as illustrative and not restrictive, the scope of the invention being indicated by the appended claims rather than by the foregoing description, and all changes which come within the meaning and range of equivalency of the claims are therefore intended to be embraced therein.

We claim as our invention:

1. A lead assembly for implantation in a patient, the assembly comprising:

a catheter adapted for insertion into a chamber of the patient's heart having a proximal end and a distal end and a lumen extending therethrough from said proximal end to said distal end thereof;

an electrode slidingly received within said lumen at said distal end of said catheter, a coil conductor having at least one wire attached to said electrode and being disposed within said lumen and adapted to transmit electrical impulses between the electrode and said proximal end of said catheter, said coil conductor having an inside diameter;

fixation means for securing said electrode to the lining of the heart chamber, the fixation means being adapted to fit within the lumen of said catheter;

a wire coil attached to said electrode, said coil having an inside diameter smaller than said inside diameter of said coil conductor and said wire coil is disposed along said at least one wire of said coil conductor; and a stylet having a distal end and a threaded segment at said distal end thereof, said threaded segment being adapted to engage said wire coil, whereby said wire coil can be displaced into said coil conductor by said threaded segment of said stylet, thereby disengaging said stylet by expanding said inner diameter of said wire coil, said wire coil being restored to its original inner diameter after removal of said threaded segment from said wire coil.

2. The lead assembly according to claim 1 wherein the fixation means comprises a helix.

3. The lead assembly according to claim 2 further comprising means for preventing the helix from rotating with respect to said catheter.

4. The lead assembly according to claim 3 wherein the rotation preventing means comprise an hexagonal inner surface on the catheter and a mating hexagonal outer surface on the electrode.

5. The lead assembly according to claim 1 wherein said threaded segment on said stylet comprises a coiled wire secured to said stylet.

6. The lead assembly according to claim 5 wherein the fixation means comprises a helix.

7. The lead assembly according to claim 6 further comprising means for preventing the helix from rotating with respect to said catheter.

8. The lead assembly according to claim 7 wherein the rotation preventing means comprise an hexagonal inner surface on the catheter and a mating hexagonal outer surface on the electrode.

9. A lead for implantation in a patient, the lead comprising:

a catheter adapted for insertion into a chamber of the patient's heart having a proximal end and a distal end and a lumen extending therethrough from said proximal end to said distal end thereof;

an electrode slidingly received within said lumen at said distal end of said catheter, a coil conductor extending from said proximal end of said catheter to said electrode and having at least one wire attached to said electrode and being disposed within said lumen and adapted to transmit electrical impulses between the electrode and said proximal end of said catheter, said coil conductor having an inside diameter and defining an axis;

fixation means attached distally to said electrode for securing said electrode to the lining of the heart chamber, the fixation means being adapted to fit within the lumen of said catheter; and a wire coil segment attached proximally to said electrode, said coil segment having an inside diameter smaller than said inside diameter of said coil conductor and having an axis parallel to said axis of said coil conductor, and being disposed along said at least one wire of said coil conductor, said wire coil segment forming a female thread within said coil conductor.

10. The lead assembly according to claim 9 wherein the fixation means comprises a helix.

11. The lead assembly according to claim 10 further comprising means for preventing the helix from rotating with respect to said catheter.

12. The lead assembly according to claim 11 wherein the rotation preventing means comprise an hexagonal inner surface on the catheter and a mating hexagonal outer surface on the electrode.

* * * * *